(12) United States Patent
Hofstraat

(10) Patent No.: US 6,951,760 B2
(45) Date of Patent: Oct. 4, 2005

(54) DIAGNOSTIC NEODYMIUM(III), YTTERBIUM(III), OR ERBIUM(III) ION-LIGAND COMPLEXES

(76) Inventor: Johannes Willem Hofstraat, Vloeteind 6, 5502 Veldhoven (NL)

( * ) Notice: Subject to any disclaimer, the term of this patent is extended or adjusted under 35 U.S.C. 154(b) by 47 days.

(21) Appl. No.: 09/380,336
(22) PCT Filed: Feb. 4, 2000
(86) PCT No.: PCT/EP98/01287
§ 371 (c)(1), (2), (4) Date: Nov. 23, 1999
(87) PCT Pub. No.: WO98/39654
PCT Pub. Date: Sep. 11, 1998

(65) Prior Publication Data
US 2002/0187563 A1 Dec. 12, 2002

Related U.S. Application Data
(60) Provisional application No. 60/042,354, filed on Mar. 24, 1997.

(30) Foreign Application Priority Data
Mar. 3, 1997 (EP) .................................... 97200615

(51) Int. Cl.[7] ................................................ G01N 21/76
(52) U.S. Cl. .......................... 436/172; 435/6; 435/7.1; 435/7.92; 435/7.94; 435/968; 435/969; 435/971; 436/501; 436/518; 436/536; 436/538; 436/546; 436/164; 436/166; 436/172; 422/82.08
(58) Field of Search .......................... 435/6, 7.1, 7.21, 435/7.92–7.95, 810, 968, 969, 971, 930, 960, 546, 164, 172, 56, 807, 808; 436/501, 518, 536, 538, 546, 164, 172, 82, 83, 56, 800; 422/82.08, 50, 52, 52.08, 55; 536/23.1, 24.1, 24.3

(56) References Cited

U.S. PATENT DOCUMENTS
4,352,751 A 10/1982 Wieder et al. .......... 260/112 R
(Continued)

FOREIGN PATENT DOCUMENTS
WO 96/00901 1/1996 .......... G01N/33/53

OTHER PUBLICATIONS
P.G. Sammes et al., "Modern Bioassays using Metal Chelates as Luminescent Probes", Natural Product Reports, vol. 13, No. 1, pp. 1–28 (1996).
(Continued)

Primary Examiner—Christopher Chin
Assistant Examiner—Gailene R. Gabel
(74) Attorney, Agent, or Firm—Knoble Yoshida & Dunleavy, LLC

(57) ABSTRACT

The invention relates to a method for detection of an analyte in a test sample by a specific binding reaction among the analyte, a specific binding partner for the analyte, and an (immuno)reactant provided with a label, characterized in that the label is a lanthanide ion-ligand complex wherein the lanthanide ion is neodymium(III) ion ($Nd^{3+}$), ytterbium(III) ion ($Yb^{3+}$), or erbium(III) ion ($Er^{3+}$) and the ligand comprises or is in contact with a sensitizing moiety which absorbs in the 400–1000 nm region, and preferably in the 400–800 nm region. Further, a diagnostic kit is disclosed as well as a method of detecting an analyte in a matrix of biomedical interest through an oligonucleotide, an antigen, or an antibody attached to a material, preferably core-shell latex or with specific binding sites wherein the antigen or antibody is labeled with the lanthanide ion-ligand complex and brought into contact with the analyte, after which the analyte with the lanthanide-ion complex is immobilized on the material, and, optionally, residual lanthanide-ion complex is removed, after which the sample obtained is irradiated with light in the 400–1000 nm region, and the emitted light from said sample is detected if said analyte is present in the matrix of biomedical interest.

5 Claims, 1 Drawing Sheet

U.S. PATENT DOCUMENTS

| | | | |
|---|---|---|---|
| 5,312,922 A | 5/1994 | Diamandis | 546/156 |
| 5,587,394 A | 12/1996 | Morgan et al. | 514/185 |
| 5,656,433 A * | 8/1997 | Selvin et al. | 435/6 |
| 5,696,240 A * | 12/1997 | Vallarino et al. | 534/15 |
| 5,830,769 A * | 11/1998 | Wieder et al. | 436/536 |
| 5,891,656 A * | 4/1999 | Zarling et al. | 435/792 |
| 6,159,686 A * | 12/2000 | Kardos et al. | 435/6 |

OTHER PUBLICATIONS

Derwent Patent Abstract 96–0866153 (1996).
Derwent Patent Abstract 96–085967 (1996).
Derwent Patent Abstract 99–264270 (1999).
Chemical Abstracts, vol. 110, 204714 (1988).
Derwent Patent Abstract 92–110885 (1992).
Chemical Abstracts, vol. 105, 164071 (1986).

* cited by examiner

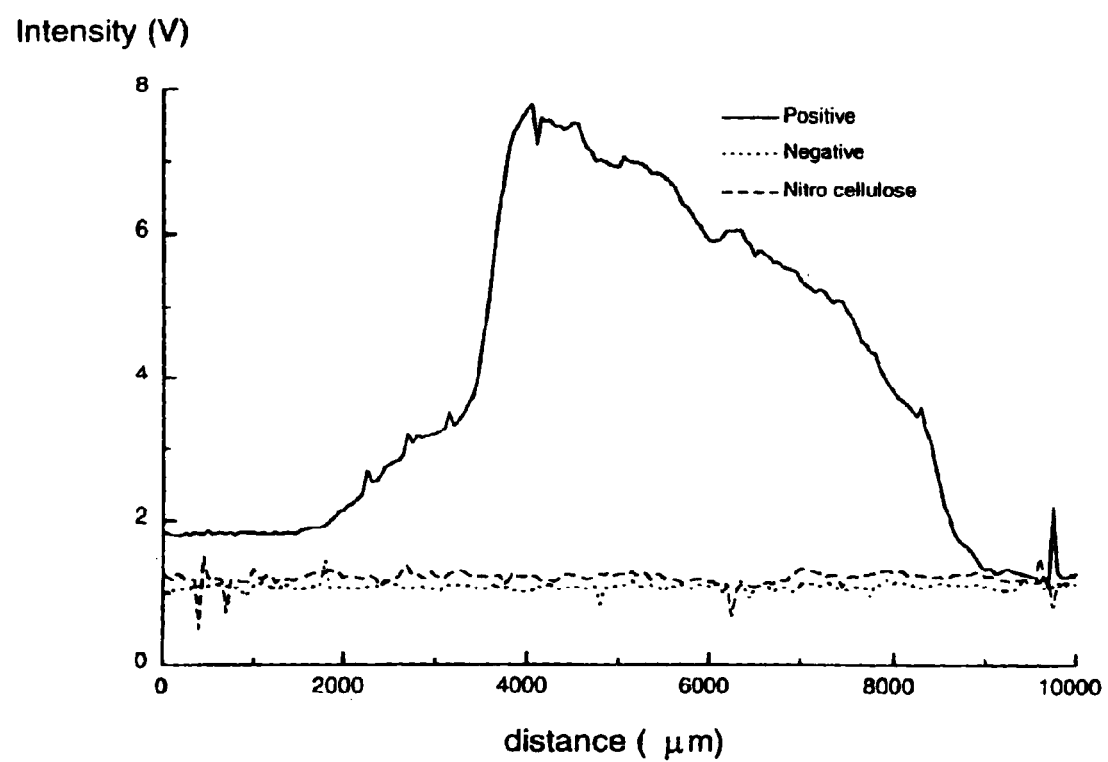
FIGURE I

DIAGNOSTIC NEODYMIUM(III), YTTERBIUM(III), OR ERBIUM(III) ION-LIGAND COMPLEXES

This application is a 371 of PCT/EP98/01287, filed Feb. 28, 1998, and claims the benefit of Provisional Application No. 60/042,354, filed Mar. 24, 1997.

BACKGROUND OF THE INVENTION

The invention pertains to lanthanide ion-ligand complexes, in particular to neodymium(III) ion ($Nd^{3+}$), ytterbium(III) ion ($Yb^{3+}$), or erbium(III) ion ($Er^{3+}$) ligand complexes, to the use of said lanthanide ion-ligand complexes for the manufacture of a diagnostic kit, to a diagnostic kit comprising the same, and to a method of detecting an analyte in a matrix of biomedical interest.

The use of metal chelates as luminescent probes is well-known in the art, and the use of such probes for diagnostic purposes has recently been commercialized, while the state of the art of the technique has been reviewed by P. G. Sammes and G. Yahioglu in *Natural Product Reports,* Vol. 13, pp. 1–28 (1996). Europium and terbium ions (Eu(III) and Tb(III), respectively), both members of the rare-earth lanthanide metals, are very suitable as luminescent probes because of their long-lived luminescence, which allows for interference-free detection. By using a time delay between excitation pulse and detection optimized for the rare-earth ion, short-lived scatter and background luminescence from the matrix can be effectively removed. Since the absorption coefficients of rare-earth ions are extremely low (1–10 $I.mole^{-1}.cm^{-1}$) direct excitation is very inefficient. In general, excitation therefore requires the aid of a chromophore as sensitizer. For Tb(III) and Eu(III) ions, which emit in the visible part of the spectrum, sensitizers requiring UV excitation have to be applied as a result of energy constraints (the triplet state of the sensitizer should be at least 1000 $cm^{-1}$ above the accepting state of the lanthanide ion). The other lanthanides in chelated forms in solution which exhibit luminescence in the visible part of the spectrum are gadolinium, samarium, and dysprosium ions. The other members of the lanthanide metals are considered to be unsuitable as luminescent probes because they have much smaller gaps between the excited states and the ground state. When used as a luminescent probe, the lanthanides are coordinated to form complexes with ligands, which complexes often are unstable in aqueous solutions.

Attempts have been made to obtain stable chelates of Eu(III) and Tb(III) ions, for instance, as disclosed in WO 96/00901 wherein complexes of Eu(III) and Tb(III) ions with polynuclear heterocyclic aromatic compounds are described. These chelate-lanthanide complexes may be applied as labels or probes for diagnostics, and are capable of intense luminescence in the visible region. A drawback to these Eu(III) and Tb(III) ion-chelates, however, is the need to sensitize them at a relatively short wavelength (UV or near-UV), which requires expensive lasers. Moreover, the excitation energy used regularly interferes with the biological material which is used for diagnostic purposes, which more often than not is sensitive to light of the UV region. Further it is of advantage to have a metal ion which exhibits a long lifetime in the excited state, which requires minimization of quenching and back-transfer.

In Russian patent applications SU 1340087 and SU 1621720 ytterbium porphyrin complexes have been disclosed, which are used to enhance the contrast coefficient in in vivo luminescent investigations of malignant tissues in animals. These complexes are not suitable as diagnostic assays for detection of specific analytes, because they do not contain an (immuno)-reactant for attachment to said analyte. Further, these complexes are hardly soluble and have poor stability in water.

SUMMARY OF THE INVENTION

It has now been found that when a lanthanide ion-ligand complex comprises neodymium(III) ion ($Nd^{3+}$), ytterbium (III) ion ($Yb^{3+}$), or erbium(III) ion ($Er^{3+}$) as the lanthanide ion, and the ligand comprises or is in contact with a sensitizing moiety which absorbs in the 400–1000 nm region, and preferably in the 400–800 nm region, the complex displays long-lived near-IR luminescence without having the disadvantages of the prior art methods. These lanthanide ion-ligand complexes further comprise an (immuno)-reactant for attachment to an analyte.

When the ligand is in contact with the sensitizing moiety, it may be covalently or ionogenically bonded, or the ligand may be in such close vicinity to the sensitizing moiety that energy transfer between the lanthanide ion-ligand complex and the sensitizing moiety is possible.

BRIEF DESCRIPTION OF THE DRAWINGS

FIG. 1 is line scan across spot on nitrocellulose membrane.

DESCRIPTION OF THE PREFERRED EMBODIMENTS

These lanthanide ion-complexes can make use of inexpensive 400–1000 nm lasers or other light sources, emit luminescence in the near-IR spectrum, have long luminescence lifetimes, high sensitivity, and good stability with respect to the irradiated light and towards the solvents used, especially towards aqueous solutions.

More specifically, the lanthanide ion-complexes according to this invention have long luminescence lifetimes and do emit in the near-IR spectrum, which leads to "zero-interference" detection (necessary for diagnostic purposes). Further, the lanthanide ion-complexes according to this invention very efficiently quench the excited triplet state of the sensitizer, which is a major source of singlet oxygen leading to photo-oxidative damage, and therefore enhance stability.

In this respect luminescence is light which is emitted by a compound upon excitation by any means, among them irradiation of laser light.

Luminescence lifetime is the time in which the luminescence emission intensity has decayed to 1/e of its original value.

Luminescence quenching is the process which leads to radiationless deactivation of the luminescent excited state, for instance, as a result of collisions of the excited molecules with species which accept energy from the excited state and dispose of it non-radiatively.

The ligand comprises a complexing moiety which shields the ion from quenching by solvent molecules, in particular water which is generally present in bioassays and contains the OH moiety with particular quenching ability, and provides strong binding of the ion and an anchor for attachment to the (immuno)reactant. The attachment of the (immuno) reactant to the lanthanide ion-ligand complex can be performed by the conventional methods well-known in the art. The ligand further comprises a sensitizing moiety, which is efficiently excited and able to transfer energy to the lanthanide.

The sensitizing moiety should be as close to the ion as possible to make the energy transfer process more efficient. Alternatively, the ligand may be a complex forming moiety which is in contact with, but not bonded to the sensitizer.

Preferably, the sensitizer comprises a site which can act as the complexing moiety. The sensitizing moiety may be any sensitizing moiety that absorbs light in the visible or near-IR range of the spectrum, i.e. between about 400 and 1000 nm, and more preferably between about 400 and 800 nm. Preferably, the sensitizing moiety is selected from fluorescein derivatives such as fluorexon, eosin, erythrosin, fluorescein, rose bengal, calcium green, and oregon green; triphenylmethane derivatives such as methylthymol blue, xylenol orange, brilliant blue, methyl green, and malachite green; porphyrin derivatives; rhodamine derivatives such as rhodamine 6G, tetrabromo-rhodamine, and lissamine; phenothiazine derivatives such as thionin and methylene blue; phenoxazine derivatives such as nile blue; coumarin derivatives; acridin derivatives such as acridin orange; (thio)indigo derivatives; carbocyanine derivatives; squaraine derivatives; and (na)phthalocyanine derivatives.

These compounds and derivatives are well-known to those skilled in the art. Coumarin derivatives, for instance, include 2- and 4-coumarins such as coumarin 120, 124, 445, 450, 490, 500, 503, and trifluoromethylcoumarin. Other sensitizers which absorb in the visible region can also be employed.

The ligand may be a composition comprising any compound comprising oxygen, nitrogen, phosphorous, or sulfur moieties which have complexing ability towards Nd(III), Yb(III), or Er(III) ions, in particular polyaminocarboxylic acid, pyridinedicarboxylic acid (dipicolinic acid, DPA), or a derivative thereof, and a sensitizer selected from fluorescein derivatives such as fluorexon, eosin, erythrosin, fluorescein, rose bengal, calcium green, and oregon green; triphenylmethane derivatives such as methylthymol blue, xylenol orange, brilliant blue, methyl green, and malachite green; porphyrin derivatives; rhodamine derivatives such as rhodamine 6G, rhodamine B, tetrabromo-rhodamine, and lissamine; phenothiazine derivatives such as thionin and methylene blue; phenoxazine derivatives such as nile blue; coumarin derivatives; acridin derivatives such as acridin orange; (thio)indigo derivatives; carbocyanine derivatives; squaraine derivatives; and (na)phthalocyanine derivatives.

Suitable polyaminocarboxylic acids are, for instance, ethylenediamine tetraacetic acid (EDTA), diethylenetriamine pentaacetic acid (DPTA), and triethylenetetraamine hexaacetic acid (TTHA), all basically comprising the aminocarboxylate groups as complexing moieties. These compounds have excellent solubility and stability in water.

The complexes which are suitable for application as near-IR luminescent long-lived diagnostic labels will, preferably, comprise a functional group which allows the attachment of the compound to an (immuno)reactant, e.g., an isothiocyanate, activated ester (such as N-hydroxysuccinimidyl ester), epoxide, or maleimide group for coupling to amino groups, an amino group for coupling to epoxides, a maleimide or halogenoacetamide group for coupling to thiol groups, a hydrazide group for coupling to aldehydes, and so on.

It has further been found that only neodymium(III) ion ($Nd^{3+}$), ytterbium(III) ion ($Yb^{3+}$), and erbium(III) ion ($Er^{3+}$) exhibit luminescence in the near-IR range of the spectrum ($\lambda_{lum,max}$=800–1600 nm) with relatively long luminescence lifetimes ($\tau_{lum}$). In this respect the erbium(III) ion ($Er^{3+}$) is less preferred, because although it exhibits relatively long luminescence lifetimes ($\tau_{lum}$). the luminescence is red-shifted to $\lambda_{lum,max}$=1530 nm (see Tables I and II), which is unfavorable because water absorbs at this wavelength, and also in view of the expensive detectors which are required for detection at 1530 nm.

TABLE I

Luminescence of $Ln^{3+}$-fluorexon complexes in $D_2O$ (as solvent; conc. $10^{-6}$M; $\lambda_{exc}$ = 500 nm), unless indicated differently:

| $Ln^{3+}$ | $\lambda_{lum,max}$ (nm) | $\tau_{lum}$ ($\mu$s) |
|---|---|---|
| Present invention: | | |
| neodymium | 880, 1060, 1320 | 0.3 |
| neodymium ($H_2O$) | 880, 1060, 1320 | 0.06 |
| ytterbium | 980 | 6.0 |
| ytterbium ($H_2O$) | 980 | 1.0 |
| erbium | 1530 | 2.5 |
| erbium ($H_2O$) | nd[a] | nd |
| Reference examples: | | |
| praseodymium | nd | nd |
| samarium | nd | nd |
| europium | nd | nd |
| gadolinium | nd | nd |
| terbium | nd | nd |
| dysprosium | nd | nd |
| holmium | nd | nd |
| thulium | nd | nd |

[a]nd = not detectable

TABLE II

Luminescence of $Ln^{3+}$-DTPA-fluorescein complexes and $Ln^{3+}$-DTPA-eosin complexes in $H_2O$ and $D_2O$ (conc. $10^{-6}$M; $\lambda_{exc}$ = 500 nm):

| $Ln^{3+}$ | $\tau_{lum}$ ($\mu$s) in $D_2O$ | $\tau_{lum}$ ($\mu$s) in $H_2O$ |
|---|---|---|
| DTPA-fluorescein: | | |
| neodymium | 0.5 | 0.16 |
| ytterbium | 1.0 | 0.61 |
| erbium | 1.0 | n.d. |
| DTPA-eosin: | | |
| neodymium | 0.5 | 0.15 |
| ytterbium | 1.0 | 0.6 |
| erbium | 1.0 | n.d. | n.d. = not detectable

The lanthanides other than neodymium, ytterbium, and erbium do not give luminescence above the detection limit for excitation at 500 nm.

The advantages of the present invention are evident. The near-IR luminescent complexes enable the design of low-cost detection devices. For excitation visible light can be used which can be obtained from inexpensive light sources such as solid-state lasers, light-emitting diodes, or flash lamps. For emission from ytterbium and neodymium silicon based detectors can be used, and expensive quartz optics are not required.

The near-IR luminescent complexes experience less interference from background signals originating from the sample solution and/or the detection optics, since visible excitation results in less scatter and less background luminescence. Moreover, the luminescence lifetime of the near-IR luminescent complexes is about two orders of magnitude shorter than that of the prior art $Eu^{3+}$ and $Tb^{3+}$ complexes. On the other hand, the luminescence lifetime of the near-IR luminescent ions is long enough to apply time-gated detection of their emission in order to further reduce the interference from background signals. The shorter lifetime of the near-IR luminescence is advantageous since the flux of luminescence photons is higher, and the number of background photons can be further decreased via the application of a narrower detection gate.

The reduced absorption of the visible radiation used for excitation makes it possible to apply the labels in opaque or strongly scattering matrices, for instance, in direct in situ measurements in body fluids and tissues.

Finally, the photochemical stability of the labels towards photo-oxidation is improved, since the triplet state of the sensitizer is efficiently depleted as a result of the energy transfer to the rare-earth ion.

The invention provides a method for detecting an analyte in a test sample, such as a body fluid or tissue of human, animal, bacterial, or vegetable origin. The method is based on the reaction between the analyte and a specific binding partner for the analyte, and can be an immunoassay, an amplification assay, or hybridisation assay, such as NASBA and PCR. The reaction product formed between the analyte and its specific binding partner is detected with a lanthanide ion-ligand complex according to the present invention, which is coupled to an (immuno)reactant. This (immuno) reactant is a compound capable of binding, directly or indirectly, the analyte or the specific binding partner for the analyte. The method can be performed according to different test formats, such as competitive or sandwich types of assays, which are well-known in the art. In the sandwich type of assay the specific binding partner can be immobilized on a solid phase. Various types of solid phases have been described, preferably polymer based core-shell latex particles or carrier materials (preferably porous carrier materials) are used. Examples are glass, membranes (e.g., nitrocellulose), and polymeric or ceramic (e.g., porous metaloxide) thin films.

According to a further feature of the invention, a kit is provided for the qualitative or quantitative determination of an analyte in a test sample, said kit comprising:

a specific binding partner for the analyte, a lanthanide ion-ligand complex provided with a labeled (immuno)reactant, enabling the specific binding partner for the analyte to be coupled to a solid phase.

It is also possible to attach both the specific binding partner and the (immuno)reactant labeled with the lanthanide ion-ligand complex to a solid phase such as a porous carrier material, in which process the specific binding partner is immobilized on said carrier and the labeled (immuno) reactant is coupled to said carrier in such a way that it is freely mobile in said carrier upon contact with test liquid or wash fluid. Such a type of test is comparable with so-called dipstick tests, which are well-known in the art.

Measurement of the lanthanide ion-ligand complexes can be performed by excitation in the visible light range with inexpensive light sources such as solid-state lasers, light emitting diodes, or flash lamps, and detection of the emission by, for example, silicon based detectors. Such light sources and detectors can be used in combination with the device described above.

It is therefore another object of the present invention to provide an apparatus comprising said kit in combination with a light source in the 400–1000 nm range, for instance a light emitting diode, and a detector which is suitable for detecting luminescence in the 800–1600 nm range, preferably the 800–1100 nm range, for instance a silicon or germanium based detector.

In accordance with the present invention, a wide variety of analytes can be measured, including antigens, antibodies, (glyco)proteins, peptides, oligonucleotides, nucleic acids, enzymes, haptens, and polysaccharides.

Specific binding partners for the analyte can be selected from antibodies, antigens, lectins, (oligo)nucteotides, receptors, and substrates.

Examples of components which specifically interact with each other are lectins and sugars, enzymes and substrates, biotin and avidin, DNA and cDNA, RNA and cRNA, DNA and RNA, PNA and RNA, PNA and PNA, PNA and DNA, ligands and receptors, RNA being m-RNA or r-RNA.

The (immuno)reactant is a reactant which is capable of specifically binding to the analyte or specific binding partner for the analyte. The (immuno)reactant can be selected from one of the analytes or specific binding partners as specified above. Specific examples are an oligonucleotide, an antibody, an anti-antibody, and protein A.

The invention is further illustrated in the examples. Examples of Direct Interaction Type Complexes: Sensitizers with Complexing Ability Towards Rare-earth Ions

EXAMPLE 1

Fluorexon was commercially obtained and used without further purification. The lanthanide ions were added from stock solutions of $YbCl_3.6H_2O$, $NdCl_3.6H_2O$, and $ErCl_3.6H_2O$ in $D_2O$ or $H_2O$. Fluorexon, a well-known fluorescence indicator for $Ca^{2+}$ ions, was used to sensitize the near-IR (NIR) emission of trivalent ytterbium, neodymium, and erbium ions. Its absorption spectrum was similar to that of fluorescein, with an absorption maximum at 490 nm.

Solutions were prepared consisting of $5 \times 10^{-6}$ M of the fluorexon and an equimolar amount of lanthanide ions ($Yb^{3+}$, $Nd^{3+}$, or $Er^{3+}$) in $D_2O$ at pD 7. The pD was carefully controlled using an ISFET-based pH meter and concentrated solutions of DCl and NaOD.

The NIR luminescence excitation spectra of the respective $Nd^{3+}$ and $Er^{3+}$ complexes are identical to the spectrum of the fluorexon/$Yb^{3+}$ complex, and all match the corresponding absorption spectra, with an excitation maximum at 490 nm. These results indicate that energy transfer from the fluorexon to the lanthanide ion is the dominant route to the observed rare-earth ion NIR luminescence and that this process is several orders of magnitude more efficient than direct excitation of the lanthanide. In the used concentration range no luminescence was observed when an absorption band of the rare-earth ion was excited.

EXAMPLE 2

Methylthymol blue was commercially obtained and used without further purification. The lanthanide ions were added from stock solutions of $YbCl_3.6H_2O$, $NdCl_3.6H_2O$ and $ErCl_3.6H_2O$ in $D_2O$ and $H_2O$. Methylthymol blue (MTB) was demonstrated to be a luminescence sensitizing agent for ytterbium(III), which emits light in a band around 1000 nm.

Solutions of $Yb^{3+}$ or $Er^{3+}$ $1 \times 10^{-5}$ M and $1 \times 10^{-5}$ M MTB in $D_2O$ (pD 5) and $H_2O$ (pH 5) were prepared. When ytterbium or erbium ions were added to the solution of MTB, the color changed from yellow to blue, which indicates the formation of a complex between MTB and the ion. The spectra in $H_2O$ are similar, but the luminescence is less intense due to more efficient quenching of the $Yb^{3+}$ excited state by $H_2O$.

MTB does not sensitize Nd(III). This was demonstrated in an experiment where both fluorexon (see Example 1) and MTB were brought into contact with $Nd^{3+}$ ions. From the absorption spectrum it was clear that both complexed MTB and fluorexon were present, but in the luminescence excitation spectrum (emission at 1060 nm, the principal $Nd^{3+}$ emission line) only fluorexon sensitization was observed.

EXAMPLE 3

Synthesis of 2',7'-dichloro-4',5'-fluorexon-4-isothiocyanate a) 4-Nitrophthalic acid (100.1 g, 0.47 mole) and 4-chlororesorcinol (135.2 g, 0.94 mole) were heated to 240° C. for 5 h, and the water formed during the reaction was removed by distillation. After cooling to room temperature, the red glass-like solid was ground to a fine powder, which was suspended in 1 M HCl (2 l) and refluxed for 1 h. After cooling to room temperature, the solid was filtered off, dried in a vacuum oven, and refluxed with acetic anhydride (1 l) for 2 h. After cooling to room temperature, the excess acetic acid and the excess acetic anhydride were removed under reduced pressure, and the residue was purified by column chromatography (silica gel, eluents dichloromethane). The product was further purified by crystallization from acetic acid (4 times, 1 g/10 ml). Yield 37.0 g (70 mmole, 15%) of 2',7'-dichlorofluorescein diacetate.

b) 2',7'-Dichloro-4-nitrofluorescein diacetate (10.7 g, 20 mmole) and paraformaldehyde (53.3 g) were heated to 110° C. in 105 ml of hydrogen bromide in acetic acid (33%). After 2 h stirring, the reaction mixture was cooled to room temperature, and acetic anhydride (150 ml) was added dropwise. The reaction mixture was then refluxed for 1 h, cooled, and the excess solvents were removed in vacuo. The yellow solid was dissolved in 75 ml of dichloromethane and precipitated in hexane (1200 ml). After filtration, the solids were dried under reduced pressure. Yield: 4',5'-(dibromomethyl)-2',7'-dichloro-4-nitrofluorescein diacetate (11.6 g, 16 mmole, 81%).

c) 4',5'-(Dibromomethyl)-2',7'-dichloro4-nitrofluorescein diacetate (16.0 g, 22 mmole) and iminodiacetic acid dimethyl ester (50.5 g) were dissolved in 225 ml of dichloromethane and stirred at room temperature for 90 h. The precipitate was filtered off, and the filtrate was precipitated in diethyl ether (750 ml). The solids were filtered off, dissolved in dichloromethane (75 ml), and precipitated in methanol (750 ml). The white solid was filtered off and dried under reduced pressure. 2',7'-Dichloro-4-nitro-4',5'-fluorexon diacetate tetramethyl ester was obtained as a white solid (12.0 g, 15 mmole, 69%).

d) 2',7'-Dichloro-4-nitro-4',5'-fluorexon diacetate tetramethyl ester (3.6 g, 4.5 mmole) was suspended in 250 ml of methanol and 10 ml of 50% sodium hydroxide solution, and the reaction mixture was stirred for 16 h at room temperature. Water was added until a clear red solution was obtained. This solution was acidified with 1M hydrochloric acid until a red precipitate was formed, which was filtered off. The 2',7'-dichloro-4-nitro-4',5'-fluorexon (3.3 g, 4.5 mmole, 99%) was obtained after drying in vacuo.

e) 2',7'-Dichloro-4-nitro-4',5'-fluorexon (1.0 g) was dissolved in 0.6 M NaOH (12 ml) and heated to reflux. Sodium sulfide:sodium hydogensulfide (0.32 M: 0.64 M, respectively) solution (10 ml) was added, and the reaction was refluxed for another 15 min. After cooling to room temperature, acetic acid was added until gas formation was finished. The reaction mixture was acidified with 30 ml of 1M hydrochloric acid. The solids were filtered off, and the filtrate was concentrated in vacuo. The residue was dissolved in water (30 ml) and concentrated again to remove traces of acid. The residue was suspended in acetone (30 ml) and filtered. The solids were collected and dried under reduced pressure. The yield of crude 2',7'-dichloro-4-amino-4',5'-fluorexon was 2.12 g (contains sodium chloride). The product was further purified by preparative HPLC (eluents: water:acetonitrile:formic acid 77.5:22.5:0.1 over a Partisil CCS C8 column). The thus purified product was dissolved in water (pH 8.4). The absorption spectrum shows a maximum at 502 nm ($\epsilon_{502}$=8.3 $10^4$ l/mole.cm).

f) 2',7'-Dichloro-4-amino-4',5'-fluorexon (50.1 mg) was dissolved in 8.0 ml of NaOH (1.40 mg NaOH/ml) solution. This solution was further diluted with 8 ml of a water:acetone (1:3) mixture. The resulting clear red solution was added dropwise under vigorous stirring to a mixture of $CSCl_2$ (2.0 ml) and acetone (2.0 ml). After stirring for 30 min, all solvents were removed in vacuo. The yield of crude 2',7'-dichloro-4',5'-fluorexon-4-isothiocyanate was 95.9 mg (contains sodium chloride and water). Purity (HPLC): 79%.

Absorption maximum 504 nm ($D_2O$; pD 8.4; $\epsilon_{504}$ (corrected for impurities) 5.7 $10^4$ l/mole.cm). Chelates of the lanthanide ions of Nd(III), Yb(III), and Er(III) were prepared by dissolving 2',7'-dichloro-4',5'-fluorexon4-isothiocyanate and an equimolar amount of the lanthanide chloride in dry dimethylsulfoxide. The NIR luminescence spectra obtained showed the sensitized excitation of the lanthanide ions with an excitation maximum of 508 nm. The luminescence emission maxima were 880 nm, 1060 nm, and 1320 nm for Nd(III) ion, 980 nm for Yb(III) ion, and 1530 nm for Er(III) ion.

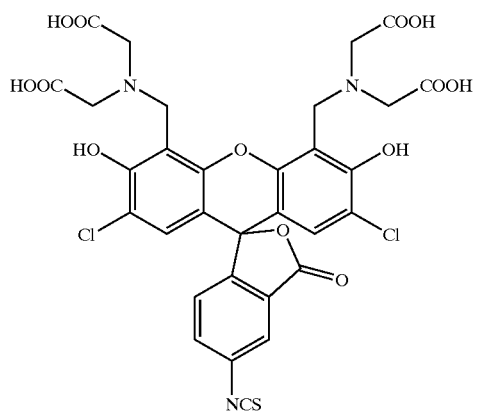

2',7'-dichloro-4',5'-fluorenxon-4-isothiocyanate

EXAMPLE 4

The 2',7'-dichloro-4',5'-fluorexon-4-isothiocyanate of Example 3 was dissolved in dry dimethylsulfoxide and an equimolar amount of $YbCl_3.6H_2O$ was added. By measurement of the near-IR luminescence of the Yb(III) ion, excited at 518 nm in the main absorption band of the dichlorofluorexon sensitizer unit, it was established that a 1:1 complex of chelate and Yb (FXTC-Yb) had been formed.

To 3.7 ml of a-hCG 293 PA (IG content 3.3 mg/ml) was added 0.37 ml of 1M carbonate buffer (prepared by adding a solution of 1.06 g of sodium carbonate in 10 ml of NEN class 1 water to a solution of 0.84 g of sodium hydrogencarbonate in 10 ml of NEN class 1 water until a pH of 9.0 was reached). The solution was distributed over 3 vials, each containing 3.9 mg ($2.4 \cdot 10^{-8}$ mole) of a-hCG. To the three vials were added 97.5 µl, 195 µl, and 390 µl of the 2.5. $10^{-3}$ M solution of FXTC-Yb in dimethyisulfoxide; i.e., a 10-fold, 20-fold, and 40-fold excess of label. The mixtures which were obtained were incubated in the dark overnight at a temperature of 4° C. Subsequently, the contents of the vials were put on Pharmacia PD-10 columns, which had been conditioned with 25 ml of DOE-buffer (consisting of 3.029 g of Tris, 1.875 g of sucrose, 3.75 g of potassium chloride, 1.25 g of dextran 15, and 0.25 g of casein in approx. 200 ml of water NEN class 1, brought to pH 8.8 with 1 M HCl, and finally brought to a final volume of 250 ml with water NEN class 1). The columns were eluted with 2.5 ml DOE-buffer. The eluted, purified, and labelled a-hCG in DOE-buffer was collected and transferred to a series of vials, each containing 250 µl of solution, which were conserved at −20° C.

The loading of the conjugate of a-hCG with the FXTC-Yb chelate was determined via an absorption measurement. For the three series of vials a loading varying from 5 to 15

FXTC-Yb labels per antibody was measured, depending on the amount of FXTC-Yb applied.

A nitrocellulose membrane was spotted with 0.5 µl of a-hCG 147B and dried overnight. Subsequently, a mixture of 5000 IU (0.75 mg; 3.8. $10^{-13}$ mole) hCG and an excess of a-hCG 293 PA (2.0. $10^{-12}$ mole), loaded with $3.0.10^{-11}$ mole of FXTC-Yb chelate, was incubated for 15 min. Part of the mixture (20 µl) was applied on the membrane and eluted with 100 µl of DOE-buffer, so that the labeled hCG could interact with the a-hCG spot on the membrane. The result of the sandwich immunoassay was established by scanning the membrane through the focal point of a 488 nm argon-ion laser, which illuminated a small area of the membrane through a mechanical chopper (385 Hz), a <510 nm reflective dichroic beam splitter positioned at 45° with respect to the laser beam in epifluorescence mode, and a 20×0.40 objective.

The emitted light was focussed onto a liquid nitrogen cooled germanium detector (NorthCoast EO-817L, bias voltage 250V) through the same objective, the 510 nm long-pass dichroic, and a 830 nm long pass cut-off filter. The signal was amplified with a lock-in amplifier (Stanford Instruments) and fed to a PC. The scan showed a low background in the order of 1 V for the nitrocellulose and the negative (no hCG present) sample, and a clear signal, significantly enhanced to 8 V, for the positive sample with hCG (see Figure I).

EXAMPLE 5

The dichlorofluorexonisothiocyanate of Example 3 was dissolved in dry dimethylsulfoxide, and an equimolar amount of $YbCl_3.6H_2O$ was added. By measurement of the near-IR luminescence of the Yb(III) ion, excited at 518 nm in the main absorption band of the dichlorofluorexon sensitizer unit, it was established that a chelate (FXTC-Yb) had been formed.

To 50 µl of a solution of 1.24 mM amino-functionalized HIVQa oligonucleotide, consisting of 24 nucleotides (60 nmole), 0.5 ml of 0.1M carbonate buffer (pH 9.0) were added. To this solution 110 µl of the $2.5.10^{-3}$ M solution of FXTC-Yb in dimethylsulfoxide were added, which is a 4-fold excess of label. The mixtures which were obtained were incubated in the dark at room temperature for 40 h, and brought to pH 5 with an acetate buffer. Subsequently, ethanol was added and the solution was cooled to −70° C. for 0.5 h, after which a pink precipitate was obtained, which was isolated after centrifugation and removal of the colored supernatant. With this product the precipitation procedure was repeated. Again a pink precipitate was obtained after precipitation, but this time the supernatant was clear. The purified and labelled oligonucleotide was conserved at −20° C. in acetate buffer.

The efficiency of labelling of the oligonucleotide with the FXTC-Yb chelate was determined via an absorption measurement. The absorption of the solution at 520 nm which is the absorption maximum of the FXTC-Yb label, was 0.100, and the absorption at 280 nm was 0.440. For free FXTC-Yb: $\epsilon_{280}$=6984 l/mole.cm and $\epsilon_{518}$=56964 l/mole.cm. For free oligonucleotide: $\epsilon_{280}$=280,000 l/mole.cm. The labelling efficiency of oligonucleotide with FXTC-Yb was calculated to be about 100%.

A Whatman Anotec porous aluminum oxide membrane (with 200 nm diameter capillary pores) was purified ultrasonically for 0.5 h in MilliQ ultrapure water. Subsequently, the membrane was thoroughly rinsed with MilliQ water, after which the membrane was activated in a solution of 0.4 M nitric acid for 2 h, and thoroughly rinsed with MilliQ water. To ensure effective cleaning of the pores the membrane was put onto a glass filter, which was connected to a water jet filter pump. The rinsed membrane was dried for 1 h at 60° C. under vacuum. A solution of 100 µl of 3-glycidyloxypropyltrimethoxy-silane in 7.5 ml of dried toluene was prepared and brought in contact with the activated membrane. The membrane covered with the solution was incubated overnight at 60° C. Subsequently, the excess of solvent was removed, and the membrane was washed first with dried toluene, and subsequently with acetone. The with epoxy-groups modified Anotec membrane was dried at 50° C. under vacuum.

This membrane was spotted with a concentration series of HIVQa-c oligonucleotides with amino end groups (the nucleotide sequence of which is complementary to that of the HIVQa oligonucleotides labelled with FXTC-Yb). The oligonucleotides were incubated for 1 h. The unbound oligonucleotides were remove by washing with 1 ml of wash fluid. Subsequently, the membrane was dried for 30 min at 37° C.

This membrane was brought into contact with 75 µl of the solution with HIVQa oligonucleotide labelled with FXTC-Yb. The incubation time was 2 h at room temperature. Following the incubation, the unbound HIVQa-FXTC-Yb oligonucleotide was removed by washing with 10 ml of washing fluid. The result of the hybridisation assay was established by scanning the membrane through the focal point of a 488 nm argon-ion laser, which illuminated a small area of the membrane through a mechanical chopper (385 Hz), a <510 nm reflective dichroic beam splitter, positioned under 45° with respect to the laser beam in epifluorescence mode, and a 20×0.40 objective. The emitted light was focussed onto a liquid nitrogen cooled germanium detector (NorthCoast EO-817L, bias voltage 250V), through the same objective, the 510 nm long-pass dichroic, and a 830 nm long pass cut-off filter. The signal was amplified with a lock-in amplifier (Stanford Instruments) and fed to a PC. Examples of Indirect Interaction Type Complexes: Sensitizers Attached to Compounds with Complexing Ability Towards Rare-earth Ions Polyaminocarboxylic acids (such as ethylenediamine tetraacetic acid, EDTA, diethylenetriamine pentaacetic acid, DTPA, and triethylenetetraamine hexa-acetic acid, TTHA) form stable complexes with lanthanide ions. As examples, sensitizer-modified derivatives of DTPA have been obtained by reaction of its commercially available dianhydride (DTPAA) with an amine. Dye derivatives which absorb in the visible part of the spectrum, like fluorescein and eosin, have been used as amine. The products thus obtained form stable complexes with lanthanides ($Yb^{3+}$, $Nd^{3+}$, $Er^{3+}$), which give intense NIR luminescence upon irradiation with visible light, even in aqueous solution,

EXAMPLE 6

DTPAA and 5-aminofluorescein were commercially obtained and used without further purification. The lanthanide ions were added from stock solutions of $YbCl_3.6H_2O$, $NdCl_3.6H_2O$ and $ErCl_3.6H_2O$ in $D_2O$ and $H_2O$.

A solution of 15 mg (1.5×0.56 mmole) of water in 0.5 ml of DMSO was added dropwise to a stirred suspension of 200 mg (1×0.56 mmole) of DTAA in 2 ml of DMSO. After 1 h, 5-aminofluorescein (100 mg, 0.5×0.56 mmole) was added. The reaction mixture was allowed to stand overnight at ambient temperature.

The mother liquor was poured into 30 ml of a triethylammoniumacetate (TEAAc) buffer (0.05 M, pH 6.5), and from this solution the AMFLU-DTPA was isolated by means of preparative HPLC over a $C_{18}$-column. A buffer (TEAAc, 0.05 M, pH6.5)/acetonitrile (MeCN) gradient was applied: 0–5 min 10% MeCN, 5–30 min 10–70% MeCN, 30–32 min 70–100% MeCN, 32–37 min 100% MeCN, 37–40 min 100–0%. The flow rate was 8 ml/min. For detection use was made of either a diode array-detector or absorbance at a fixed wavelength near the absorption maximum of fluorescein.

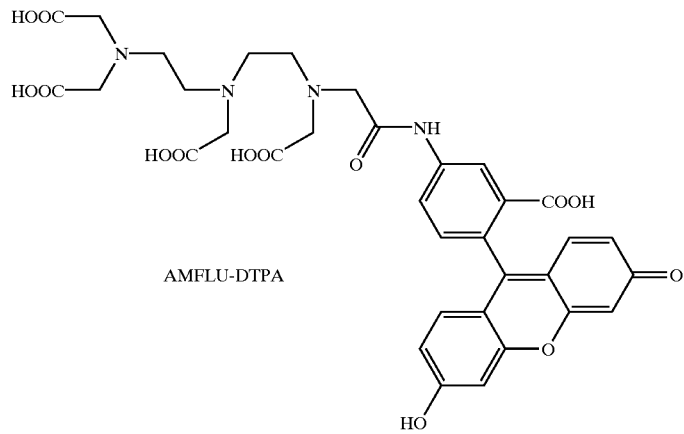

AMFLU-DTPA

The fraction at approx. 20 minutes having the typical fluorescein absorption spectrum was collected and concentrated by vacuum evaporation of the eluent. The product precipitated after adding 0.3 M HCl. The yellow powder, AMFLU-DTPA, was collected by centrifugation and washed with dilute acid and acetonitrile.

All spectroscopic measurements were carried out in buffered $D_2O$ (0.01M Tris/DCl, pD 8). Complex concentrations were in the range $2-5\times10^{-6}$ M.

A titration experiment in which the 1060 nm photoluminescence intensity was measured as a function of the $Nd^{3+}$-ligand ratio proved the 1:1 complexation of lanthanide ions with this ligand. The NIR luminescence excitation spectrum (emission at 1060 nm) of the 1:1 AMFLU-DTPA/$Nd^{3+}$ complex perfectly matched the absorption spectrum of the ligand, indicating efficient sensitization of the lanthanide emission by the fluorescein moiety.

Also the $Yb^{3+}$ and $Er^{3+}$ complexes were prepared by simply mixing stock solutions of the lanthanide ion and AMFLU-DTPA. The NIR luminescence spectra were recorded with an excitation wavelength of 490 nm, the absorption maximum of fluorescein. They all showed the sensitized lanthanide luminescence.

Spectra obtained for the complexes clearly showed the sensitizing properties of fluorescein: the emission of trivalent ytterbium, neodymium, and erbium at their typical emission wavelengths could be observed when excited at 490 nm, the absorption maximum of fluorescein. In addition, the luminescence excitation spectrum of the Nd(III) emission (at 1060 nm) and the ytterbium emission (at 980 nm) have been recorded and were an excellent match of the absorption (and excitation) spectrum of fluorescein.

EXAMPLE 7

DTPAA was commercially obtained and used without further purification. 5-aminoeosin was commercially purchased. The lanthanide ions were added from stock solutions of $YbCl_3.6H_2O$, $NdCl_3.6H_2O$ and $ErCl_3.6H_2O$ in $D_2O$ and $H_2O$.

The procedure for the preparation of AMFLU-DTPA was repeated using 5-aminoeosin instead of 5-aminofluorescein and yielded AMEO-DTPA, which has its absorption maximum at 515 nm.

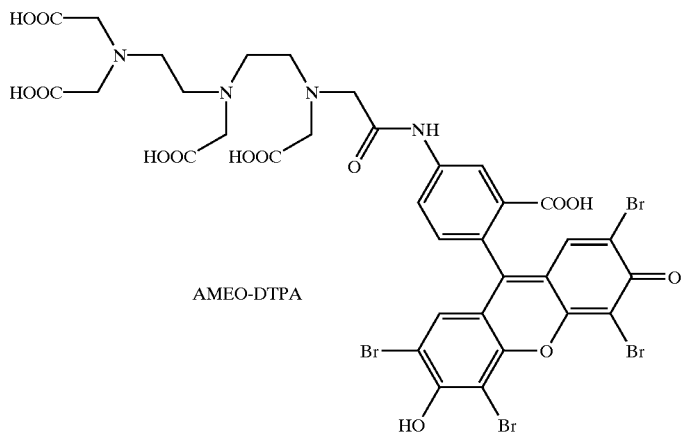

AMEO-DTPA

The 1:1 complexation was confirmed in an experiment similar to that used in Example 1. The luminescence excitation and emission spectra of AMEO-DTPA/Ln$^{3+}$ complexes were recorded under the same conditions as the corresponding AMFLU-DTPA complexes and showed similar photophysical characteristics. For the Nd$^{3+}$ and Yb$^{3+}$ complexes, luminescence was also observed in H$_2$O (Tris/HCl, pH 8).

General: Characterization Methods

Spectroscopic Measurements

Steady state luminescence measurements were performed on a PTI Alphascan spectrofluorimeter, using a 75-W quartz-tungsten-halogen lamp followed by a SPEX 1680 double monochromator for excitation and a PTI 0.25-m single monochromator for separation of the emitted light, detected under an angle of 90°. The emitted light was converted into an electric signal with a Northcoast 817L liquid nitrogen cooled Germanium detector. For detection a lock-in amplifier (SRS530) was applied; the excitation light was modulated at 70 Hz with an optical chopper. For time-resolved luminescence measurements an Edinburgh Analytical Instruments LP900 system was used, which consisted of a pulsed Xe-lamp followed by a 0.25 m monochromator for excitation and another 0.25 m monochromator positioned at an angle of 90° with respect to the first for separation of the emitted light. The photons were converted into electric signals by means of a Northcoast 817P liquid nitrogen cooled germanium detector (lifetimes >250 ns) or, alternatively, via a Hamamatsu R2658 thermoelectrically cooled photomultiplier tube (lifetimes<250 ns), and fed to a Tektronix fast digital oscilloscope.

What is claimed is:

1. A method for detection of an analyte in a test sample comprising the steps of:

preparing a lanthanide ion-ligand complex by mixing a lanthanide ion and a ligand, wherein the lanthanide ion is selected from the group consisting of neodymium (III) ion, ytterbium (III) ion (Yb3+) and erbium (III) ion (Er$^{3+}$), and wherein said ligand is bonded to a sensitizing moiety, which absorbs light in the 400–1000 nm region;

labeling a reactant or immunoreactant with the lanthanide ion-ligand complex by contacting the reactant or immunoreactant with the lanthanide ion-ligand complex to form a labeled reactant or immunoreactant;

mixing an analyte, a specific binding partner for the analyte, and the labeled reactant or immunoreactant to form a mixture, whereby the analyte will bind with the the specific binding partner for the analyte and with the labeled reactant or immunoreactant;

separating the unbonded lanthanide ion ligand complexes:

irradiating the mixture with light having a wavelength ranging from 400 nm to 1000 nm;

measuring an emitted luminescence from the complexes in said mixture formed by binding of said analyte, said specific binding partner, and said labeled reactant or immunoreactant; and detecting the analyte using said luminescence measurement.

2. The method as claimed in claim 1, wherein the lanthanide ion is selected from the group consisting of neodymium (III) ion (Nd$^{3+}$) and ytterbium (III) (Yb$^{3+}$).

3. The method as claimed in any one of claims 1 and 2, wherein the sensitizing moiety is selected from the group consisting of fluorescein derivatives; triphenylmethane derivatives; porphyrin derivatives; rhodamine derivatives; phenothiazine derivatives; phenoxazine derivatives; coumarin derivatives; acridin derivatives; thio-indigo derviatives; indigo derivatives; carbocyanine derivatives; squaraine derivatives; naphthalocyanine derivatives; and phthalocyanine derivatives.

4. The method as claimed in claim 1, wherein the ligand is a composition which comprises, as one of its constituents, a compound which comprises an element selected from the group consisting of oxygen nitrogen, phosphorous, and sulfur moieties which complexes with Nd (III), Yb (III), or Er (III) ions, and the sensitizing moiety is selected from the group consisting of fluorescein derivatives; triphenylmethane derivatives; porphyrin derivatives; rhodamine derivatives; phenothiazine derivatives; phenoxazine derivatives; coumarin derivatives; acridin derivatives: thio-indigo derivatives; indigo derivatives; carbocyanine derivatives; squaraine derivatives; naphthalocyanine derivatives and; phthalocyanine derivatives.

5. The method of claim 4, wherein the compound is selected from the group consisting of polyaminocarboxylic acid, pyridine dicarboxylic acid, and a derivative thereof.

* * * * *